(12) United States Patent
Rozema et al.

(10) Patent No.: US 7,682,626 B2
(45) Date of Patent: Mar. 23, 2010

(54) POLYVINYLETHERS FOR DELIVERY OF POLYNUCLEOTIDES TO MAMMALIAN CELLS

(75) Inventors: David B. Rozema, Madison, WI (US); Darren Wakefield, Fitchburg, WI (US)

(73) Assignee: Roche Madison Inc., Madison, WI (US)

( * ) Notice: Subject to any disclaimer, the term of this patent is extended or adjusted under 35 U.S.C. 154(b) by 738 days.

(21) Appl. No.: 10/772,502

(22) Filed: Feb. 5, 2004

(65) Prior Publication Data

US 2004/0156909 A1 Aug. 12, 2004

Related U.S. Application Data

(60) Provisional application No. 60/445,635, filed on Feb. 7, 2003.

(51) Int. Cl.
| | |
|---|---|
| A61K 9/127 | (2006.01) |
| A61K 31/70 | (2006.01) |
| C12N 15/00 | (2006.01) |
| C12N 15/88 | (2006.01) |
| A01N 43/04 | (2006.01) |

(52) U.S. Cl. .................. 424/450; 435/455; 435/458; 514/44

(58) Field of Classification Search ............... None
See application file for complete search history.

(56) References Cited

U.S. PATENT DOCUMENTS

| | | | |
|---|---|---|---|
| 6,383,811 B2 | 5/2002 | Wolff et al. | |
| 6,616,946 B1 * | 9/2003 | Meier et al. | 424/489 |
| 2003/0026841 A1 * | 2/2003 | Trubetskoy et al. | 424/486 |

OTHER PUBLICATIONS

Merdan et al (Prospects for cationic polymers in gene and oligonucleotide therapy against cancer, Advanced Drug Delivery Reviews, 2002. 54:715-758).*
Akhtar S et al. "The delivery of antisense therapeutics." Adv Drug Deliv Rev; 2000 vol. 44 No. 1 pp. 3-21.
Budker V et al. "Naked DNA delivered intraportally expresses efficiently in hepatocytes." Gene Therapy; 1996 vol. 3 No. 7 pp. 593-598.
Carrasco L "Entry of animal viruses and macromolecules into cells." FEBS Lett; 1994 vol. 350 No. 2-3 pp. 151-154.
Cheung CY et al. "A pH-sensitive polymer that enhances cationic lipid-mediated gene transfer." Bioconjug Chem; 2001 vol. 12 No. 6 pp. 906-910.
Ghosh C et al. "Intracellular delivery strategies for antisense phosphorodiamidate morpholino oligomers." Antisense Nucleic Acid Drug Dev; 2000 vol. 10 No. 4 pp. 263-274.
Han S et al. "Water-soluble Lipopolymer for Gene Delivery." Bioconjug Chem 2001 vol. 12 pp. 337-345.
Kyriakides TR et al. "pH-sensitive polymers that enhance intracellular drug delivery in vivo." J Control Release; 2002 vol. 78 No. 1-3 pp. 295-303.
Lackey CA et al. "Hemolytic Activity of pH-Responsive Polymer-Streptavidin Bioconjugates." Bioconjugate Chem; 1999 vol. 10 No. 3 pp. 401.
Lackey et al. "A biomimetic pH-responsive polymer directs endosomal release and intracellular delivery of an endocytosed antibody complex." Bioconjug Chem. 2002 vol. 13 No. 5 pp. 996-1001.
Murthy N et al. "The design and synthesis of polymers for eukaryotic membrane disruption." J Control Release 1999 vol. 61 pp. 137-143.
Oku N et al. "A novel non-viral gene transfer system, polycation liposomes." Adv Drug Deliv Rev 2001 vol. 21 pp. 209-218.
Plank C et al. "Application of membrane-active peptides for drug and gene delivery across cellular membranes." Adv Drug Deliv Rev 1998 vol. 34 No. 1 pp. 21-35.
Plank C. et al. "The influence of endosome-disruptive peptides on gene transfer using synthetic virus-like gene transfer systems." J Biol Chem 1994 vol. 269 No. 17 pp. 12918-12924.
Robaczewska MS et al. "Inhibition of hepadnaviral replication by polyethylenimine-based intravenous delivery of antisense phosphodiester oligodeoxynucleotides to the liver." Gene Ther; 2001 vol. 8 No. 11 pp. 874-881.
Tonge SR et al. "Responsive hydrophobically associating polymers: a review of structure and properties." Adv Drug Deliv Rev 2001 vol. 53 pp. 109-122.
Zhang G et al. "High Levels of Foreign Gene Expression in Hepatocytes after Tail Vein Injections of Naked Plasmid DNA." Human Gene Therapy 1999 vol. 10 No. 10 pp. 1735-1737.
Zhang X et al. "In vivo gene delivery via portal vein and bile duct to individual lobes of the rat liver using a polylysine-based nonviral DNA vector in combination with chloroquine." Hum Gene Ther, 2001 vol. 12 No. 18 pp. 2179-2190.

* cited by examiner

*Primary Examiner*—Janet L Epps-Smith
(74) *Attorney, Agent, or Firm*—Kirk Ekena

(57) ABSTRACT

A class of polymers for delivery of polynucleotides to cells in described. More specifically, amphiphilic polyvinylethers and compositions containing amphiphilic polyvinylethers are described.

15 Claims, 4 Drawing Sheets

POLYVINYLETHERS FOR DELIVERY OF POLYNUCLEOTIDES TO MAMMALIAN CELLS

CROSS-REFERENCE TO RELATED APPLICATIONS

This application is related to prior U.S. Provisional Application Ser. No. 60/445,635 filed Feb. 7, 2003.

FIELD OF THE INVENTION

This invention relates to polymers and compositions for the delivery of polynucleotides to cells. Amphiphilic polyvinylether polymers are described.

BACKGROUND OF THE INVENTION

The route of cellular entry for most conventional drugs is diffusion across the biological membrane. For this reason, drugs tend to be small (MW<500) and amphipathic, containing both hydrophobic and hydrophilic functionalities. These characteristics engender molecules with water solubility, while allowing them to cross the nonpolar lipid bilayer of the cell membrane. In contrast, the drugs used in antisense and gene therapies are relatively large hydrophilic polymers and are frequently highly negatively charged as well. Both of these physical characteristics preclude their direct diffusion across the cell membrane. For this reason, the major barrier to gene therapy and antisense therapy is the delivery of the drug to the cellular interior. This situation is in contrast to standard drug development in which the identification of the drug is the major barrier in development.

Gene or polynucleotide transfer to cells is an important technique for biological and medical research as well as potentially therapeutic applications. The polynucleotide needs to be transferred across the cell membrane and into the cell. Gene transfer methods currently being explored include viral vectors and non-viral methods.

Viral delivery was first accomplished with mouse retroviruses. However, these vectors cannot infect all cell types efficiently, especially in vivo. Therefore, several viral vectors, including Herpes virus, Adenovirus, Adeno-associated virus and others are being developed to enable more efficient gene transfer different cell types.

For non-viral delivery, polynucleotides can be incorporated into lipid vesicles (liposomes) or complexed with polymers. Other non-viral methods of polynucleotide delivery to cells include electroporation and "gene gun" technologies. One of the several methods of polynucleotide delivery to cells is the use of polynucleotide/polycation complexes. It has been shown that cationic proteins, like histones and protamines, or synthetic polymers, like polylysine, polyarginine, polyomithine, DEAE dextran, polybrene, and polyethylenimine may be effective intracellular polynucleotide delivery agents.

Polycations facilitate nucleic acid condensation. Multivalent cations with a charge of three or higher have been shown to condense DNA. These include spermidine, spermine, $Co(NH_3)_6^{3+}$, $Fe^{3+}$, and natural or synthetic polymers such as histone H1, protamine, polylysine, and polyethylenimine. Analysis has shown DNA condensation to be favored when 90% or more of the charges along the sugar-phosphate backbone are neutralized.

The volume which one polynucleotide molecule occupies in a complex with polycations is much lower than the effective volume of the free polynucleotide molecule. The size of a polynucleotides/polymer complex is probably critical for gene delivery in vivo and possible for in vitro as well. For intravascular delivery, the polynucleotide needs to cross the endothelial barrier in order to reach the parenchymal cells of interest. The largest endothelial fenestrae (holes in the endothelial barrier) occur in the liver and have an average diameter of 100 nm. The trans-epithelial pores in other organs are much smaller. For example, muscle endothelium can be described as a structure which has a large number of small pores with a radius of 4 nm, and a very low number of large pores with a radius of 20-30 nm. The size of the polynucleotide complexes is also important for the cellular uptake process. After binding to the cells the polynucleotide/polycation complex is likely taken up by endocytosis. Since endocytic vesicles have a typical internal diameter of about 100 nm, polynucleotide complexes smaller than 100 nm are preferred. The compacted form of the condensed polynucleotide/polycation complexes also protects the polynucleotide from nuclease degradation, both in serum and in acidic intracellular environments.

Polycations may provide attachment of polynucleotides to the cell surface. The polymer forms a cross-bridge between the polyanionic polynucleotide and the polyanionic surface of a cell. As a result, the mechanism of polynucleotide translocation to the intracellular space might be non-specific adsorptive endocytosis. Polycations also provide a convenient linker for attaching specific ligands to the complex, thereby allowing targeting to specific cell types.

Polymers can also facilitate cellular entry of polynucleotides. For instance, some polymers, such as polyethylenimine, are thought to probably disrupt endosomal/lysosomal function through a proton sponge effect. Disruption of endosomal/lysosomal function has also been accomplished by linking endosomal or membrane disruptive agents such as fusion peptides or adenoviruses to the polycation or complex. Polymers that are pH-sensitive have found broad application in the area of drug delivery because of their ability to exploit various physiological and intracellular pH gradients for the purpose of controlled release of drugs. pH sensitivity can be broadly defined as any change in polymer's physico-chemical properties over a range of pH. Narrower definitions demand significant changes in the polymer's ability to retain or release a bioactive substance in a physiologically tolerated pH range (typically pH 5.5-8).

SUMMARY OF THE INVENTION

In a preferred embodiment, we describe polyvinylether polymers for delivery of polynucleotides to cells. The polynucleotide may be a DNA, RNA or synthetic polynucleotides. The cell may be in vitro or in vivo. A preferred polyvinylether is an amphiphilic polyvinylether. The polyvinylether polymers may contain monomer subunits selected from the list comprising: alkyl vinylethers, positively charged vinylethers, negatively charged vinylethers, aryl vinylethers, and polyethyleneglycol-containing vinylethers.

In a preferred embodiment, we describe polymeric transfection agents comprising: polyvinylether polymers. The copolymerization of alkyl vinylether monomers and amine-protected vinylether monomers yields amphiphilic cationic polymers that can be used to deliver polynucleotides to mammalian cells. Following polymerization of the monomers, the amine protective group is removed to yield the positively charged amine.

In a preferred embodiment, we describe polymeric transfection agents comprising: polyvinylether polymers. The copolymerization of alkyl vinylether monomers and amine-protected vinylether monomers yields amphiphilic cationic polymers that can be used to deliver polynucleotides to mammalian cells. Following polymerization of the monomers, the amine protective group is removed to yield the positively charged amine.

In a preferred embodiment we describe a composition for delivering a polynucleotide to a cell comprising: a polynucleotide and a polyvinylether. In another embodiment, the composition further comprises an anionic reversibly modified polyvinylether. The polynucleotide may be associated with the polyvinylether through electrostatic interaction. Alternatively, the polynucleotide may be covalently linked to the polyvinylether. Preferably, the covalent linkage is labile.

In a preferred embodiment, we describe membrane active polymers comprising amphiphilic polyvinylethers. The polyvinylether polymers can be associated with polynucleotides to enhance delivery of the polynucleotides to cells in vitro and in vivo.

In a preferred embodiment, we describe the reversible modification of cationic polyvinylethers to form polyanions comprising: modifying amines on a polyvinylether by reaction with maleic anhydrides. A preferred maleic anhydride is a disubstituted maleic anhydride. A preferred disubstituted maleic anhydride is 2-propionic-3-methylmaleic anhydride. Exposure of the modified polyvinylether to acid results in cleavage of the anhydride modification and regeneration of the amine.

In a preferred embodiment, the functionality of the polymer may be modified or enhanced by covalent attachment of functional groups. Functional groups may be added to the polymer though copolymerization or through reaction with a reactive group, such as an amine, in the polymer.

In a preferred embodiment, we describe a process for delivering a polynucleotide to a cell comprising: covalently linking the polynucleotide to a cationic amino polyvinylether, reversible modifying amines on the polymer to carboxyl's, and contacting the cell with the polynucleotide-polyvinylether conjugate. Preferably, the polynucleotide is linked to the polyvinylether through a labile bond. A preferred linkage is through a maleic anhydride thioester. A preferred modification of amines on the polyvinylether is maleic anhydride modification.

Further objects, features, and advantages of the invention will be apparent from the following detailed description when taken in conjunction with the accompanying drawings.

DETAILED DESCRIPTION

We have synthesized amphiphilic cationic polymers that are based upon the polymerization of vinyl ethers. A vinyl ether has the general structure $R_1R_2C=CR_3OR_4$, wherein $R_1$, $R_2$, and $R_3$ may be any alkyl group, aryl group or a hydrogen, and $R_4$ may be any alkyl or aryl group but may not be hydrogen.

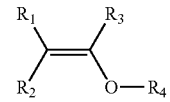

Positively charged amino groups and negatively-charged carboxylates may be incorporated into the polyvinylethers using protected monomers. For example, phthalimido-vinylethers for amino groups (FIG. 1) and ester-containing vinylethers for carboxyl groups. Other hydrophilic monomers such as polyethyleneglycol-containing vinylethers need not be protected. Hydrophobicity may be derived from the inclusion of alkyl vinylether monomers in the syntheses. Positive charge is necessary for complex formation via electrostatic (ionic) interaction with negatively charged nucleic acids. Addition of hydrophobic groups gives the polymers amphiphilic characteristics and enhances polynucleotide delivery to cells. Addition of hydrophobic groups can also provide the polymer with membrane disruptive activity.

Figure 1:
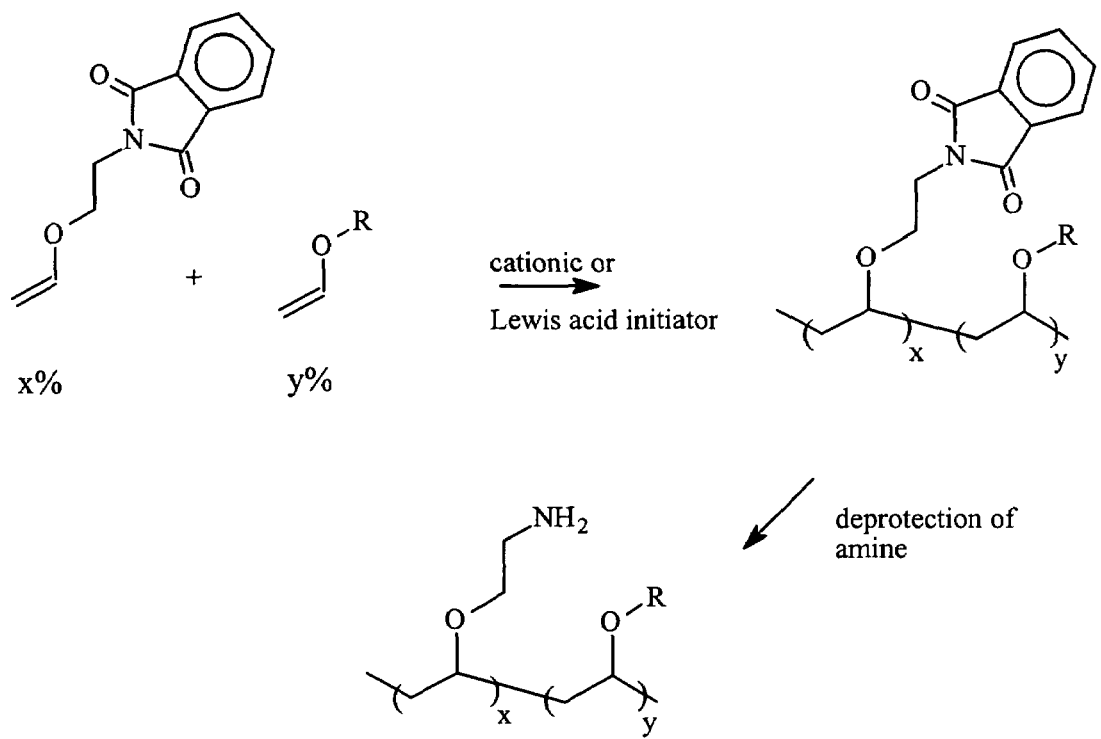
FIG. 1. Illustration of polymerization of vinyl ethers using phthalimido-vinylether to produce a polyamine. X and Y represent molar ratios of monomers used in polymerization of the random copolymer.

The polymerization may be initiated by addition of a cationic or a Lewis acid initiator (FIG. 1). The side-chains of the resulting polymer are a mixture of the starting vinylethers. In this way, polymers of varying compositions are easily synthesized from mixtures of vinylethers. Thus, the charge density and the hydrophobicity of the polyvinylether polymers are determined by the molar ratios of the particular vinyl ethers used as monomers in the synthesis. A wide variety of vinyl ethers may be used in the polymerization reaction, many of which are commercially available, including: 2-chloroethyl vinylether, 2-aminoethyl vinylether, 1,4-cyclohexanedimethanol vinylether, 1,4-butanediol vinylether, 2-ethylhexyl vinylether, 3-amino-1-propanol vinylether, 4-(vinyloxy)butyl benzoate, butyl vinylether, cyclohexyl vinylether, di(ethylene glycol) vinylether, dodecyl vinylether, ethyl vinylether, ethylene glycol butyl vinylether, isobutyl vinylether and octadecyl vinylether. In addition, many more vinyl ether monomers may be synthesized; such as 2-vinyloxy ethyl phthalimide.

Because of their positive charge, addition of these cationic polyvinylethers to polynucleic acids results in condensation of the polynucleic acid, and complex formation. Addition of these complexes to cells results in an enhancement of polynucleic acid delivery. Large nucleic acids, such as plasmid DNA, as well as oligonucleotides, such as small interfering RNA, can be delivered to cells in tissue culture (in vitro) or in vivo using these polymers.

It is also possible to deliver uncharged polynucleotides to cells using the amphiphilic cationic polyvinylethers. An uncharged polynucleotide, such as a phosphorodiamidate morpholino oligonucleotide (PMO), may be directly linked to the polymer. The conjugate is then contacted with the cell. Alternatively, the uncharged polynucleotide may be hybridized to a complementary charged polynucleotide. The negatively charged polynucleotide duplex can then interact ionically with the cationic polymer. The complex is then contacted with the cell.

While cationic polymers can effectively condense polynucleotides into nanoparticles, their cationic nature limits their utility for in vivo applications. The intravascular route of administration of polynucleotide nanoparticles can be particularly inefficient for positively charged complexes.

Decreased transfection efficiency in vivo is due in part to the interaction of the cationic polyplexes with blood components. This effect is usually attributed to the opsonization of the complexes with serum components. Toxic manifestations of systemically-administered cationic complexes can range from red blood cell agglutination to potent inflammatory reaction and elevated serum levels of liver enzymes.

Several studies have attempted to avoid such adverse interactions by including molecules such as polyethylene-glycol (PEG) in the particle to mask the positive charge. An alternative strategy is to "recharge" the polynucleotide/polycation particle to give the particle an overall negative charge (U.S. Pat. No. 6,383,811). Polynucleotides can be condensed with an excess of polycations in aqueous solutions forming complexes with positive surface charge. The charge surplus contained in the polycation/polynucleotide particles can be used to deposit a layer of polyanions on the surface surrounding the core of condensed polynucleotide. This approach enables the formation of nanoparticles that are both small (<150 nm-in-diameter) and negatively-charged. A negatively charged particle has much less non-specific interactions with negatively-charged serum and tissue constituents and can be more efficiently targeted to specific cells.

The described polycations can be converted into acid-cleavable polyanions by reacting the amine-containing polymers with maleic anhydrides. The maleamate bond is a well-studied pH-labile bond derived from the reaction of an amine and a maleic anhydride. The rate of maleamated cleavage is dependent upon the structure of the maleic anhydride used to form the maleamate. In general, disubstituted maleamates, such as Carboxylate-substituted DimethylMaleic anhydride (CDM), are more labile than monosubstituted maleamates, which are more labile than unsubstituted maleamates. Reaction of the described polyvinylether polymers with CDM reversibly converts amines on the polymers to negatively charged carboxyl groups, thus converting the polycation to a polyanion. The resultant polyanion may be used to recharge cationic polyvinylether/polynucleotide complexes. Because the bond formed between the maleic anhydride and the amine of the polymer is acid labile, exposure of this recharged complex to acid reverts the recharging process to produce a positively-charged particle and a polycation. We have found that recharged DNA nanoparticles formed with amphiphilic polyvinylether polycations and CDM-modified polyvinylether polyanions remain small and non-aggregating in physiological solutions. The hydrophobic components of the polycations and polyanions appear to provide extra stability to the complexes.

Sufficient hydrophobicity incorporated into the polyvinylether can give the polymer membrane activity. Modification of a membrane active polyvinylether by reaction with CDM can inhibition its membrane activity. Incubation of the modified polymer at acidic pH, such as in an endosome, restores membrane activity with a half-life of 10 min at pH 5.

Definitions

To facilitate an understanding of the present invention, a number of terms and phrases are defined below:

Polymer—A polymer is a molecule built up by repetitive bonding together of smaller units called monomers. A polymer can be linear, branched network, star, comb, or ladder types of polymer. A polymer can be a homopolymer in which a single monomer is used or can be copolymer in which two or more monomers are used.

The main chain of a polymer is composed of the atoms whose bonds are required for propagation of polymer length. For example in poly-L-lysine, the carbonyl carbon, α-carbon, and α-amine groups are required for the length of the polymer and are therefore main chain atoms. The side chain of a polymer is composed of the atoms whose bonds are not required for propagation of polymer length. For example in poly-L-lysine, the β, γ, δ and ε-carbons, and ε-nitrogen are not required for the propagation of the polymer and are therefore side chain atoms.

Other Components of the Monomers and Polymers: Polymers may have functional groups that enhance their utility. These groups can be incorporated into monomers prior to polymer formation or attached to the polymer after its formation. Functional groups may be selected from the list consisting of: targeting groups, interaction modifiers, steric stabilizers, and membrane active compounds, affinity groups and reactive groups.

Targeting groups—Targeting groups, or ligands, are used for targeting the polymer or polymer complex to cells, to specific cells, to tissues or to specific locations in a cell. Targeting groups enhance the association of molecules with a cell. Examples of targeting groups include those that target to the asialoglycoprotein receptor by using asialoglycoproteins or galactose residues. Other proteins such as insulin, EGF, or transferrin can be used for targeting. Other targeting groups include molecules that interact with membranes such as fatty acids, cholesterol, dansyl compounds, and amphotericin derivatives. A variety of ligands have been used to target drugs and genes to cells and to specific cellular receptors. The ligand may seek a target within the cell membrane, on the cell membrane or near a cell. Binding of a ligand to a receptor may initiate endocytosis.

Steric stabilizer—A steric stabilizer is a long chain hydrophilic group that prevents aggregation of final polymer by sterically hindering particle to particle electrostatic interactions. Examples include: alkyl groups, PEG chains, polysaccharides, hydrogen molecules, alkyl amines.

Interaction modifier—An interaction modifier changes the way that a molecule interacts with itself or other molecules, relative to molecule containing no interaction modifier. The result of this modification is that self-interactions or interactions with other molecules are either increased or decreased. For example, polyethylene glycol is an interaction modifier that decreases interactions between molecules and themselves and with other molecules.

Membrane active—Membrane active polymers or compounds are molecules that are able to alter membrane structure. This change in structure can be shown by the compound inducing one or more of the following effects upon a membrane: an alteration that allows small molecule permeability, pore formation in the membrane, a fusion and/or fission of membranes, an alteration that allows large molecule permeability, or a dissolving of the membrane. This alteration can be functionally defined by the compound's activity in at least one the following assays: red blood cell lysis (hemolysis), liposome leakage, liposome fusion, cell fusion, cell lysis and endosomal release. More specifically membrane active compounds allow for the transport of molecules with molecular weight greater than 50 atomic mass units to cross a membrane. This transport may be accomplished by either the total loss of membrane structure, the formation of holes (or pores) in the membrane structure, or the assisted transport of compound through the membrane.

Amphiphilic Compounds—Amphiphilic, or amphipathic, compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bonds. Hydrocarbons are hydrophobic groups.

Polyion—A polyion (or polyelectrolyte), is a polymer possessing charge, i.e. the polymer contains a group (or groups) that has either gained or lost one or more electrons. The term polyion includes polycations, polyanions, zwitterionic polymers, and neutral polymers. The term zwitterionic refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations. A charged polymer is a polymer that contains residues, monomers, groups, or parts with a positive or negative charge and whose net charge can be neutral, positive, or negative.

Polycation—A polycation can be a polymer possessing net positive charge, for example poly-L-lysine hydrobromide or a histone. The polymeric polycation can contain monomer units that are charge positive, charge neutral, or charge negative, however, the net charge of the polymer must be positive. A polycation also can be a non-polymeric molecule that contains two or more positive charges.

Polyanion—A polyanion can be a polymer containing a net negative charge, for example polyglutamic acid. The polymeric polyanion can contain monomer units that are charge negative, charge neutral, or charge positive, however, the net charge on the polymer must be negative. A polyanion can also be a non-polymeric molecule that contains two or more negative charges.

Polynucleotide—The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA. The term polynucleotide includes deoxyribonucleic acid (DNA) and ribonucleic acid (RNA) and combinations of DNA, RNA and other natural and synthetic nucleotides.

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell.

A polynucleotide-based gene expression inhibitor comprises any polynucleotide containing a sequence whose presence or expression in a cell causes the degradation of or inhibits the function, transcription, or translation of a gene in a sequence-specific manner. Polynucleotide-based expression inhibitors may be selected from the group comprising: siRNA, microRNA, interfering RNA or RNAi, dsRNA, ribozymes, antisense polynucleotides, and DNA expression cassettes encoding siRNA, microRNA, dsRNA, ribozymes or antisense nucleic acids. SiRNA comprises a double stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (miRNAs) are small noncoding polynucleotides, about 22 nucleotides long, that direct destruction or translational repression of their mRNA targets. Antisense polynucleotides comprise sequence that is complimentary to an gene or mRNA. Antisense polynucleotides include, but are not limited to: morpholinos, 2'-O-methyl polynucleotides, DNA, RNA and the like. The polynucleotide-based expression inhibitor may be polymerized in vitro, recombinant, contain chimeric sequences, or derivatives of these groups. The polynucleotide-based expression inhibitor may contain ribonucleotides, deoxyribonucleotides, synthetic nucleotides, or any suitable combination such that the target RNA and/or gene is inhibited.

Transfection—The process of delivering a polynucleotide to a cell has been commonly termed transfection or the process of transfecting and also it has been termed transformation. The term transfecting as used herein refers to the introduction of a polynucleotide or other biologically active compound into cells. The polynucleotide may be used for research purposes or to produce a change in a cell that can be therapeutic. The delivery of a polynucleotide for therapeutic purposes is commonly called gene therapy. The delivery of a polynucleotide can lead to modification of the genetic material present in the target cell. The term stable transfection or stably transfected generally refers to the introduction and integration of an exogenous polynucleotide into the genome of the transfected cell. The term stable transfectant refers to a cell which has stably integrated the polynucleotide into the genomic DNA. Stable transfection can also be obtained by using episomal vectors that are replicated during the eukaryotic cell division (e.g., plasmid DNA vectors containing a papilloma virus origin of replication, artificial chromosomes). The term transient transfection or transiently transfected refers to the introduction of a polynucleotide into a cell where the polynucleotide does not integrate into the genome of the transfected cell. If the polynucleotide contains an expressible gene, then the expression cassette is subject to the regulatory controls that govern the expression of endogenous genes in the chromosomes. The term transient transfectant refers to a cell which has taken up a polynucleotide but has not integrated the polynucleotide into its genomic DNA.

Transfection Agent—A transfection agent, or transfection reagent or delivery vehicle, is a compound or compounds that bind(s) to or complex(es) with oligonucleotides and polynucleotides, and mediates their entry into cells. Examples of transfection reagents include, but are not limited to, cationic liposomes and lipids, polyamines, calcium phosphate precipitates, histone proteins, polyethylenimine, polylysine, and polyampholyte complexes. It has been shown that cationic proteins like histones and protamines, or synthetic polymers like polylysine, polyarginine, polyornithine, DEAE dextran, polybrene, and polyethylenimine may be effective intracellular delivery agents. Typically, the transfection reagent has a component with a net positive charge that binds to the oligonucleotide's or polynucleotide's negative charge. The transfection reagent mediates binding of oligonucleotides and polynucleotides to cells via its positive charge (that binds to the cell membrane's negative charge) or via ligands that bind to receptors in the cell. For example, cationic liposomes or polylysine complexes have net positive charges that enable them to bind to DNA or RNA.

EXAMPLES

Example 1

Synthesis of a Vinyl Ether Monomer

2-Vinyloxy Ethyl Phthalimide was prepared via reacting 2-chloroethyl vinyl ether (25 g, 0.24 mol) and potassium phthalimide (25 g, 0.135 mol) in 100° C. DMF (75 mL) using tetra n-butyl ammonium bromide (0.5 g) as the phase transfer catalyst. This solution was heated for six hours and then crashed out in water and filtered. This solid was then recrystallized twice from methanol to give white crystals.

Example 2

Generalpolymer Synthesis

Figure 2:
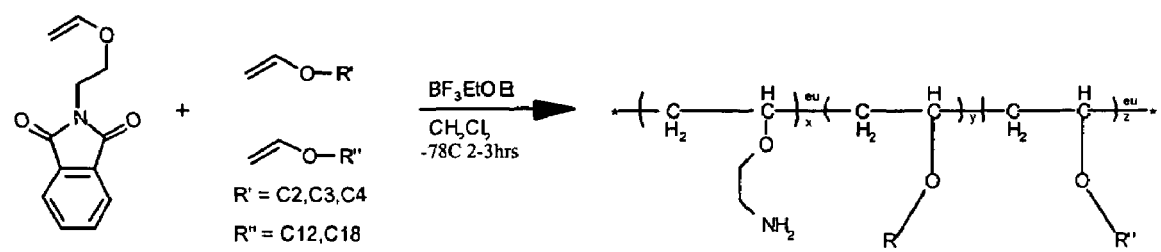
FIG. 2. Illustration of the polymerization of 2-Vinyloxy Ethyl Phthalimide, and two classes of alkyl vinylether monomers to produce an amphiphilic polyvinylether.

X mol % amine-protected vinylether (e.g., 2-Vinyloxy Ethyl Phthalimide) was added to an oven dried round bottom flask under a blanket of nitrogen in anhydrous dichloromethane. To this solution Y mol % alkyl (e.g., ethyl, propyl, butyl) vinylether was added, followed by Z mol % alkyl (dodecyl, octadecyl) vinylether. While the polymers listed in the table below were synthesized using 2-3 different monomers, the invention is not limited to a specific composition of vinyl ether monomers. Polymers comprising more monomers or different monomers were readily envisioned. The solution was brought to −78° C. in a dry ice acetone bath. To this solution 10 mol % $BF_3EtOEt$ was added and the reaction was allowed to proceed for 2-3 hours at −78° C. (FIG. 2), and then quenched with a methanol ammonium hydroxide solution. The polymer was brought to dryness under reduced pressure and then brought up in 30 ml of 1,4-dioxane/methanol (2/1). 20 mol eq. of hydrazine per phthalimide was added to remove the protecting group from the amine. The solution was refluxed for 3 hours, then brought to dryness under reduced pressure. The solid was brought up in 20 ml 0.5 M HCl, refluxed for 15 minutes, diluted with 20 ml distilled water, and refluxed for additional hour. The solution was then neutralized with NaOH, cooled to room temperature, transferred to 3,500 molecular cellulose tubing, dialyzed for 24 hrs (2×20 L) against distilled water, and freeze dried. The molecular weight of the polymers was estimated using analytical size exclusion columns according to standard procedures. While polymers containing the indicated vinyl ether monomers are described in these examples, the invention is not limited to these particular monomers.

Example 3

Synthesis of Polyvinylether Random Copolymers

The degree of hydrophobicity and charge in the polyvinylether polymers are determined the vinylether monomers present in the polymerization process. Several examples are show in the tables below.

TABLE 1

Polyvinylether based polymers

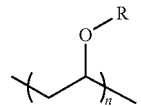

| polymer | |
|---|---|
| DW220 | R = —$(CH_2)_2NH_2$ 55%, |
|  | R = —$(CH_2)_3CH_3$ 45% |
| DW301 | R = —$(CH_2)_2NH_2$ 88%, |
|  | R = —$(CH_2)_3CH_3$ 9%, |
|  | R = —$(CH_2)_{17}CH_3$ 3% |
| DW550 | R = —$(CH_2)_2NH_2$ 50%, |
|  | R = —$(CH_2CH_2O)_3CH_3$ 45%, |
|  | R = —$(CH_2)_{11}CH_3$ 5% |
| DW559 | R = —$(CH_2)_2NH_2$ 50%, |
|  | R = —$CH_2CH_3$ 50% |
| DW560 | R = —$(CH_2)_2NH_2$ 50%, |
|  | R = —$(CH_2)_2CH_3$ 50% |
| DW561 | R = —$(CH_2)_2NH_2$ 50%, |
|  | R = —$(CH_2)_3CH_3$ 50% |
| MC741 | R = —$(CH_2)_2NH_2$ 90%, |
|  | R = —$CH_2CH_3$ 7%, |
|  | R = —$(CH_2)_{11}CH_3$ 3% |

TABLE 2

Polyvinylether based polymers

| | 2-Vinyloxyethyl Phthalimide | $C_2H_5$ | $C_3H_7$ | $C_4H_9$ | $(C_2H_2O)_2C_4H_9$ | $(C_2H_2O)_3CH_3$ | $C_{12}H_{25}$ |
|---|---|---|---|---|---|---|---|
| 536 | 87.5% | 7.5% | | | | | 5% |
| 537 | 75% | 20% | | | | | 5% |
| 538 | 50% | 45% | | | | | 5% |
| 539 | 87.5% | | | | 7.5% | | 5% |
| 540 | 75% | | | | 20% | | 5% |
| 541 | 50% | | | | 45% | | 5% |
| 542 | 87.5 | | 7.5% | | | | 5% |
| 543 | 75% | | 20% | | | | 5% |
| 544 | 50% | | 45% | | | | 5% |
| 545 | 87.5% | | | 7.5% | | | 5% |
| 546 | 75% | | | 20% | | | 5% |
| 547 | 50% | | | 45% | | | 5% |
| 548 | 87.5% | | | | | 7.5% | 5% |
| 549 | 75% | | | | | 20% | 5% |
| 557 | 95% | | | | | | 5% |
| 562 | 50% | | | | 50% | | |
| 563 | 50% | | | | | 50% | |

Example 4

Hemolysis Assay

Incorporation of hydrophobic vinylether monomers into the polymers can impart membrane activity to the polymer. The polyvinylethers may be screened for their potential membrane activity by assaying red blood cell hemolysis. Porcine whole blood was isolated in heparin-containing vacutainers. The red blood cells were isolated by centrifugation at 500 RCF for 5 min. Red blood cells were washed three times with 100 mM dibasic sodium phosphate at the desired pH, and resuspended to the initial volume. The desired pH phosphate buffer was obtained by acidification of a dibasic sodium phosphate stock with HCl. 20 µL of the washed RBC suspension, approximately $10^8$ cells, were added to 500 µL of phosphate buffer. To this solution was added 10 µg of polyvinylether polymer. The samples were then incubated for 30 min at 37° C. Red blood cells were then spun for 1 min at 15,000 RCF. Lysis was determined by measuring the absorbance of the supernatant at 541 nm. Percent hemolysis was calculated assuming 100% lysis to be the absorbance of hemoglobin released upon addition of deionized water. The ability of the polyvinylethers to lyse red blood cells is dependent on the size of the hydrophobic chain incorporated into the polymer, ie. butyl is more lytic than propyl which is more lytic than ethyl.

Example 5

Stability of DNA-Amphiphilic Polycation Complexes

The amphiphilic polyvinylethers form complexes with DNA that are stronger than complexes formed between DNA and small cationic membrane active peptides. To test the strength of the interaction between the synthesized polyvinylethers and DNA, Cy3-labeled DNA was complexed with the minimal amount of polycation required to fully condense 10 µg of DNA. The DNA-polycation polyelectrolyte complex was then displaced by adding increasing amounts of NaCl. The small cationic peptide melittin was displaced from DNA at lower concentrations of salt than were the polyvinylethers.

Example 6

Delivery of Plasmid DNA

Polyvinylethers were synthesized with various ratios of monomers according to table 1. Polymers 559-561 were then complexed with plasmid DNA encoding the luciferase gene to form particles. The dialyzed polymers were added to a solution containing 10 µg/mL plasmid DNA encoding the luciferase gene in 0.5 mL of 5 mM HEPES pH 7.5/150 mM NaCl. Polyvinylethers (DW559-561) were added to a concentration of 30 µg/mL in a total volume of 200 µl. The complexes were then added to wells containing mouse hepatocyte cells or 293 human kidney cells in Dulbecco's modified Eagle Media containing 10% fetal bovine serum. The cells were allowed to incubate for 48 h. The cells were then harvested and then assayed for luciferase expression. The amount of transfection was reported in relative light units and is the average transfection for two separate wells of cells. As a control, the same amount of DNA was transfected using the commercially available transfection reagent TransIT LT1 (Mirus Corporation) according to manufacturer's protocol.

TABLE 3

Delivery of plasmid DNA by polyvinylethers

| Transfection Reagent | Relative light units |
|---|---|
| DW559 | 969,566 |
| DW560 | 20,987,866 |
| DW561 | 27,716,194 |
| TransIT LT-1 | 26,847,738 |

Each of the polyvinylether polymers was effective in delivering plasmid DNA to cells in vitro, with the ethyl polyvinylether being the least effective of the three and the butyl polyvinylether being at least as effective as the commercially available transfection agent.

Example 7

Delivery of Uncharged Oligonucleotides to Cells

Antisense therapies hold tremendous promise for treating a wide variety of human diseases. These therapies are based on the selective inhibition of expression of a specific gene. Because they are highly specific, antisense agents could in theory have fewer side effects and display less toxicity than traditional drugs. In addition, because antisense agents exert their effects by binding to a complementary sequence in a target RNA molecule, designing antisense agents to specifically inhibit a particular RNA species is straightforward. A major factor hindering the effective use of antisense agents is the low efficiency at which these molecules are delivered to, and internalized by, cells in vivo.

Phosphorodiamidate morpholino oligonucleotides (PMO) represent a class of uncharged antisense agents. For delivery of PMOs to cells using cationic polymers, complementary nucleic acid oligonucleotides were hydridized to PMOs to generate negatively charged concatamers. These 1 µl of a 1 mM solution containing the concatamers was mixed with 50 µg polyvinylether polymer to form complexes. The complexes were then recharged with 200 µg CDM-modified polyvinylether polymers. These recharged complexes were then contacted with cells. For these experiments, a HeLa cell line that carries an integrated luciferase gene with a mutant splice site was used. The mutant splice site results in production of an mRNA coding for a truncated, inactive luciferase protein. Delivery of an appropriate PMO to these cells blocks this splice site thus enabling expression of the full-length active enzyme. The luciferase activity in this cell line is therefore directly proportional to the amount of PMO delivered to the cells. Toxicity of the delivery agent results in decreased signal. Using these cells, we found that polynucleotide/polyvinylether complexes were able to efficiently deliver PMO molecules to cells in vitro.

TABLE 4

Delivery of Concatamer Oligonucleotides

| Sample | Fold-induction of luciferase |
|---|---|
| DW301/CDM-DW301 | 12.0 |
| DW220/CDM-DW220 | 6.4 |

Fold increase in luciferase production above luciferase production in the absence of delivery reagent. In our experiments, there is no increase in luciferase upon addition of PMO alone.

Example 8

Reversible Attachment of PMO to Polymer

Figure 3:
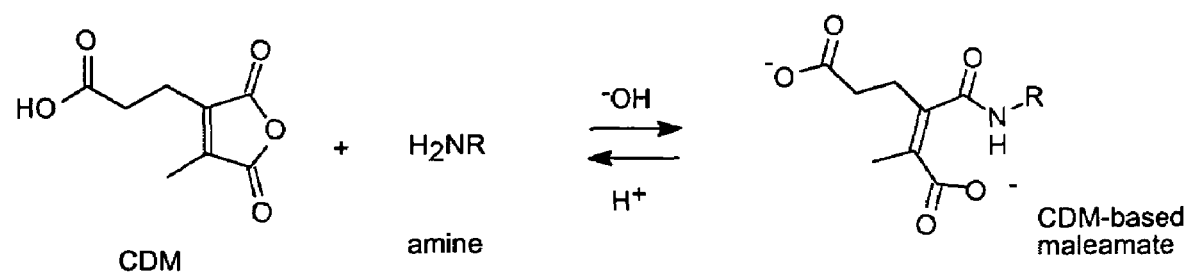
FIG. 3. Illustration of the structure of CDM and its maleamate upon acylation of an amine.

In addition to formation of nucleic acid/polymers complexes, another method for associating a polynucleotide and a polyvinylether polymer is to covalently link them together. However, in order for the polynucleotide to be active, it must be at some point released from the delivery vehicle. This release requires a labile bond that is broken after delivery. A labile bond used to facilitate delivery is a disubstituted maleamic acid, which is derived from reaction of an amine and a disubstituted maleic anhydride (FIG. 3). A disubstituted maleic anhydride, (e.g., carboxylate substituted dimethylmaleic anhydride (CDM)), can reversibly convert an amine into a carboxylate. CDM contains a maleic anhydride functional group that may be converted into a pH-labile maleamate group, and a carboxylate group, which may be used for conjugation.

In order to conjugate the oligonucleotide selectively to the carboxylate group of CDM, the carboxylate must be selectively activated to enable it to react without modification of the maleic anhydride (or vise versa). This activation is achieved using a thioester group. Compared to an anhydride, the thioester group is relatively unreactive, but will react slowly with nucleophiles such as amines. In particular, thioesters will react with amine-terminal cysteine groups via a reaction termed native chemical ligation. Native chemical ligation can occur in the presence of a variety of thiols and amines, but irreversible coupling occurs when the thiol and amine are in the same molecule, as they are in cysteine. The selective coupling occurs by formation of an intermediate thioester followed by intramolecular attack of the thioester by the amine to form an amide.

Using CDM thioester (a CDM derivative with a thioester at the distal carboxylate), it is possible to selectively react the anhydride functional group with an amine, followed by reaction with either an amine or an amine-terminal cysteine group. In this way, two molecules are attached via an acid-labile maleamate bond. For reversible attachment of a polynucleotide to a polyvinylether polymer, a PMO molecule with a primary amino terminus can be reacted with a CDM thioester molecule, The PMO-CDM can then be coupled to a an amine containing polyvinylether. 5 nmol of amino-PMO (which blocks a mutant splice site in the mutant Luciferase transcript) either bare or hybridized with a complimentary strand of DNA was reacted with nothing or with 2 μg of CDM thioester in the presence of HEPES pH 7.9. To this was added 200 μg of polymer DW550. After three hours the polymer+PMO or polymer–PMO conjugate was added to cells. HeLa Luc/705 cells (Gene Tools, Philomath OR) were grown under conditions used for HeLa cells. The cells were plated in 24-well culture dishes at a density of $3\times10^6$ cells/well and incubated for 24 hours. Media were replaced with 1.0 ml DMEM containing 2.5 nmol amino-PMO complexes. The cells were incubated for 4 hours in a humidified, 5% $CO_2$ incubator at 37° C. The media was then replaced with DMEM containing 10% fetal bovine serum. The cells were then incubated for an additional 48 h. The cells were then harvested and the lysates were then assayed for luciferase expression.

The results demonstrate enhanced delivery of the uncharged polynucleotide when it is covalently linked to the DW550 polyvinylether polymer.

TABLE 5

Delivery of Oligonucleotides by Covalent attachment

| Polyvinylether (see table 1) | Fold induction of luciferase |
|---|---|
| no attachment | |
| DW550 + PMO | 2 |
| DW550 + hybridized with DNA | 2 |
| crosslinked polycation and polyanion | |
| DW550-CDM-PMO | 7.5 |
| DW550-hybridized PMO | 10 |

Fold induction of luciferase production by 0.25 μmol PMO-NH$_2$ reversibly linked by CDM thioester to 100 μg CDM-modified polyvinylether DW550 (see table 1 for structures). No attachment control did not have CDM-thioester modification of oligonucleotide.

Example 9

Figure 4:
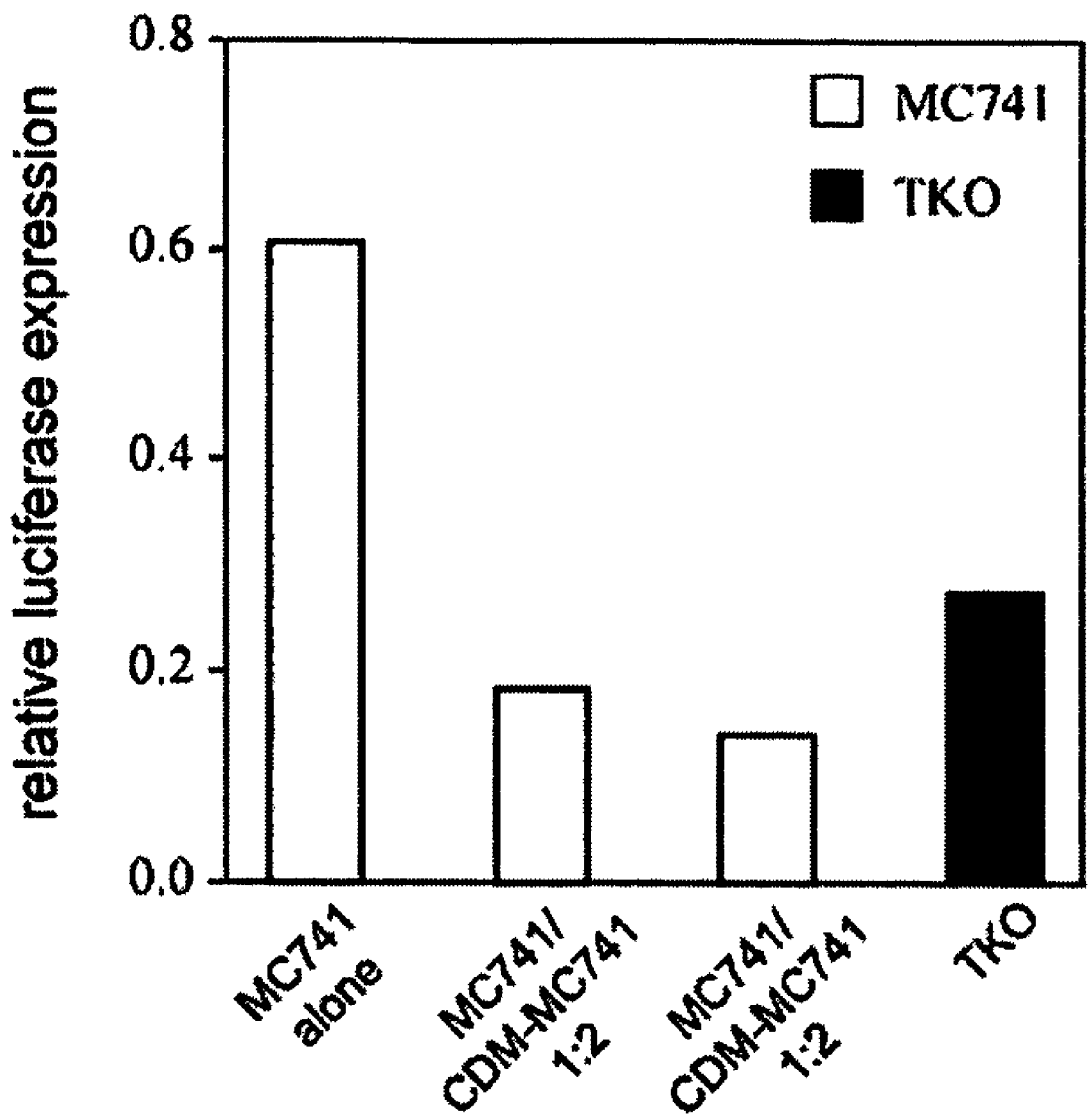
FIG. 4. Delivery of siRNA to CHO-luc cells in culture using recharged particles containing MC741 and CDM-modified MC741

Delivery of Small Interfering RNA 50 ng of siRNA targeted against luciferase was complexed with 1 μg of MC741(see example 3). To these cationic particles was added 0, 2, or 3 μg of maleamate-modified, negatively charged MC741. Similar ternary systems are effective in delivery of plasmid DNA in vitro. As a control, we compared the inhibition of luciferase from these particles to inhibition by siRNA delivered by the commercially available siRNA transfection reagent TransIT-TKO. The particles were added to a CHO cell line that stably expresses the luciferase gene. Particle formation with the membrane active polycation MC741 alone resulted in modest delivery of siRNA, as observed by a drop in luciferase expression to 60%. However, the ternary particles, containing siRNA, polyvinylether MC741 and modified polyvinylether MC741, were as effective in the delivery of the siRNA to cells as was the commercially available transfection reagent. The results are shown in FIG. 4.

Example 10

In Vivo Delivery of Polynucleotides

For in vivo delivery of polynucleotides, the following polyvinylethers were synthesized in addition to the previously described polymers. A targeting ligand galactose was attached to polyvinylether DW291 using carbodiimide coupling reagent N-(3-dimethylaminopropyl)-N'-ethylcarbodiimide and lactobionic acid (4-O-β-D-Galactopyranosyl-D-gluconic acid) to produce polymer DW297.

TABLE 6

Polyvinylether based polymers

| | |
|---|---|
| DW291 | R = —(CH$_2$)$_2$NH$_2$ 88% |
| | R = —(CH$_2$)$_{11}$CH$_3$ 2% |
| | R = —CH$_2$CH$_3$ 10% |
| DW297 | R = —(CH$_2$)$_2$NH$_2$ 58% |
| | R = —(CH$_2$)$_2$NHCO-lactobionic acid 30% |
| | R = —(CH$_2$)$_{11}$CH$_3$ 2% |
| | R = —CH$_2$CH$_3$ 10% |

TABLE 6-continued

Polyvinylether based polymers

| polymer | |
|---|---|
| DW541 | R = —(CH$_2$)$_2$NH$_2$ 50%<br>R = —CH$_2$CH$_2$O(CH$_2$)$_3$CH$_3$ 45%<br>R = —(CH$_2$)$_{11}$CH$_3$ 5% |

Delivery of DNA-polyvinylether complexes by portal vein injection. CDM-modified polymers were synthesized by reaction of the polyvinyl ether in the presence of 3 weight equivalents of CDM in the presence of 10 weight equivalents of HEPES base. Complexes were formed by addition of 10 μg of polyvinylether DW291 to 10 μg of DNA followed by addition of 30 μg of CDM-modified polyvinylether DW297. Mouse livers were exposed through a ventral midline incision, and the complexes, in 200 μl of 5 mM HEPES pH 7.5, were manually injected over approximately 30 sec into the portal vein using a 30-gauge, ½-inch needle and 1-ml syringe. In some animals, a microvessel clip was applied during the injection at the junction of the hepatic vein and caudal vena cava. Anesthesia was obtained from intramuscular injection of 1000 μg ketamine-HCl in 1 ml of normal saline and from inhalation of methoxyflurane as needed. One day after injection, the animals were sacrificed, and luciferase expression was assayed. Luciferase activity in the liver, as measured by relative light units, was 22,137.

Delivery of DNA-polydimethylformamide-polyvinylether complexes by portal vein injection.

CDM-modified polymers were synthesized by reaction of the polyvinylether with 3 weight equivalents of CDM in the presence of 10 weight equivalents of HEPES base. A polycation (pDMF) was synthesized from dimethylformamide by addition of dry HCl in ethyl ether. Complexes were formed by addition of 60 μg of pDMF to 20 μg of DNA followed by addition of 20 or 120 μg of CDM-modified polyvinylether DW297. Mouse livers were exposed through a ventral midline incision, and the complexes in 200 μl of 5 mM HEPES pH 7.5 were manually injected over approximately 30 sec into the portal vein using a 30-gauge, ½-inch needle and 1-ml syringe. In some animals, a microvessel clip was applied during the injection at the junction of the hepatic vein and caudal vena cava. Anesthesia was obtained from intramuscular injection of 1000 μg ketamine-HCl in 1 ml of normal saline and from inhalation of methoxyflurane as needed. One day after injection, the animals were sacrificed, and luciferase expression was assayed in the liver tissue.

| pDNA/pDMF/CDM-DW297<br>(μg/μg/μg) | delivery route | relative light units |
|---|---|---|
| 20/60/20 | portal vein | 212,706 |
| 20/60/120 | portal vein | 91,654 |
| 20/60/20 | hepatic artery | 139,209 |
| 20/60/120 | hepatic artery | 535,592 |

Delivery of DNA-polyvinylether complexes by tail vein injection. Complexes were formed by addition of polyvinylether DW561 to 20 μg of DNA according to following table. Tail vein injections of 0.25 mL of 5 mM HEPES pH 7.4 and isotonic glucose were preformed on ICR mice (n=3) using a 30 gauge, 0.5 inch needle. One day after injection, the livers and lungs were harvested and homogenized in lysis buffer (0.1% Triton X-100, 0.1 M K-phosphate, 1 mM DTT, pH 7.8). Insoluble material was cleared by centrifugation and 10 μl of the cellular extract was analyzed for luciferase activity.

| DNA/DW561 | relative light units | |
|---|---|---|
| (μg/μg) | liver | lung |
| 10/80 | 4,700 | 35,600 |

Delivery of DNA-polyvinylether complexes by bile duct injection. CDM-modified DW541 was synthesized by reaction of the polyvinylether with 3 weight equivalents of CDM in the presence of 10 weight equivalents of HEPES base. Complexes were formed by addition of 40 μg of polyvinylether DW541 to 20 μg of DNA followed by addition of 0 or 25 μg of CDM-modified DW541 in 200 μl of 5 mM HEPES pH 7.4. Plasmid delivery into the bile duct was performed in groups of 2 ICR mice. Ventral midline incisions were performed to expose the liver and associated vessels. The mice were anesthetized with intramuscular injections of 1000 μg of ketamine HCl and by inhalation of methoxyflurane as needed. Bile duct injections in mice were performed using manual injections with a 30-gauge, ½ inch needle and 1 ml syringe. A microvessel clip was used to occlude the bile duct downstream from the point of injection in order to prevent flow to the duodenum and away from the liver. The gallbladder inlet was not occluded. One day after injection, livers were harvested and homogenized in lysis buffer (0.1% Triton X-100, 0.1 M K-phosphate, 1 mM DTT, pH 7.8). Insoluble material was cleared by centrifugation and 10 μl of the cellular extract was analyzed for luciferase activity.

| Complex<br>(μg DNA/μg DW541/μg CDM-DW541) | relative light units |
|---|---|
| 10/40/0 | 378,500 |
| 10/40/25 | 219,800 |

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. A composition for delivery of a polynucleotide to a cell comprising:
   the polynucleotide and a cationic polyvinylether random copolymer, wherein the polyvinylether random copolymer comprises cationic monomeric units and alkyl or aryl monomeric units and is capable of lysing red blood cells.

2. The composition of claim 1 wherein the polynucleotide is associated with the polyvinylether via an electrostatic interaction.

3. The composition of claim 1 wherein the polynucleotide is associated with the polyvinylether via labile covalent linkage.

4. The composition of claim 3 wherein the polynucleotide is associated with the polyvinylether via labile maleamate covalent linkage.

5. The composition of claim 1 wherein the polynucleotide is selected from the list consisting of: DNA, plasmid DNA, linear DNA, dsDNA, ssDNA, RNA, expression cassette,
   antisense oligonucleotide, siRNA, microRNA, RNA expression cassette, ribozyme, dsRNA, and synthetic polynucleotides.

6. The composition of claim 5 wherein the polynucleotide expresses a protein.

7. The composition of claim 5 wherein the polynucleotide expresses an RNA.

8. The composition of claim 5 wherein the polynucleotide inhibits expression of a gene in the cell.

9. The composition of claim 1 wherein amines on the polyvinylether random copolymer are reversibly modified to carboxyls to convert the polyvinylether random copolymer to a labile polyanion.

10. The composition of claim 9 wherein the polynucleotide is covalently linked to the reversibly modified polyvinylether random copolymer via a labile maleamate bond.

11. The composition of claim 1 wherein the cationic monomeric units consist of amine-containing monomeric units.

12. The composition of claim 1 wherein the polyvinylether random copolymer comprises cationic monomeric units and at least two classes of alkyl or aryl monomeric units.

13. The composition of claim 12 wherein the cationic monomeric units consist of amine-containing monomeric units.

14. The composition of claim 13 wherein the alkyl monomeric units contain alkyl groups selected from the group consisting of: ethyl, propyl, butyl, dodecyl, and octadecyl.

15. A composition for delivery of a polynucleotide to a cell comprising:
   the polynucleotide, a cationic polymer, and an anionic reversibly modified polyvinylether random copolymer wherein the anionic reversibly modified polyvinylether random copolymer comprises hydrophobic monomeric units and 2-propionic-3-methylmaleic anhydride modified amine-containing monomeric units wherein:
   a) the modified polyvinylether random copolymer is not membrane active and
   b) cleavage of the 2-propionic-3-methylmaleic anhydride groups from the amine-containing monomeric units results in an unmodified polyvinylether random copolymer that is membrane active and capable of lysing red blood cells.

* * * * *